(12) United States Patent
Chen et al.

(10) Patent No.: US 10,722,173 B2
(45) Date of Patent: Jul. 28, 2020

(54) METHODS, SYSTEMS AND COMPUTER PROGRAM PRODUCTS FOR VISUALIZING ANATOMICAL STRUCTURES AND BLOOD FLOW AND PERFUSION PHYSIOLOGY USING IMAGING TECHNIQUES

(71) Applicant: East Carolina University, Greenville, NC (US)

(72) Inventors: Cheng Chen, Greenville, NC (US); Thomas Bruce Ferguson, Jr., Raleigh, NC (US); Kenneth Michael Jacobs, Greenville, NC (US); Zhiyong Peng, Greenville, NC (US)

(73) Assignee: East Carolina University, Greenville, NC (US)

( * ) Notice: Subject to any disclaimer, the term of this patent is extended or adjusted under 35 U.S.C. 154(b) by 236 days.

(21) Appl. No.: 15/518,548

(22) PCT Filed: Oct. 13, 2015

(86) PCT No.: PCT/US2015/055251
§ 371 (c)(1),
(2) Date: Apr. 12, 2017

(87) PCT Pub. No.: WO2016/061052
PCT Pub. Date: Apr. 21, 2016

(65) Prior Publication Data
US 2017/0224274 A1    Aug. 10, 2017

Related U.S. Application Data

(60) Provisional application No. 62/136,010, filed on Mar. 20, 2015, provisional application No. 62/063,673, filed on Oct. 14, 2014.

(51) Int. Cl.
*A61B 5/00*        (2006.01)
*A61B 5/026*       (2006.01)
(Continued)

(52) U.S. Cl.
CPC ............ *A61B 5/489* (2013.01); *A61B 5/0044* (2013.01); *A61B 5/0077* (2013.01);
(Continued)

(58) Field of Classification Search
CPC ... A61B 5/0044; A61B 5/0071; A61B 5/0077; A61B 5/0086; A61B 5/0261;
(Continued)

(56) References Cited

U.S. PATENT DOCUMENTS 4,541,433 A    9/1985   Baudino
5,058,596 A    10/1991  Makino et al.
(Continued)

FOREIGN PATENT DOCUMENTS

CN    101784227 A    7/2010
CN    102083362 A    6/2011
(Continued)

OTHER PUBLICATIONS

International Search Report and the Written Opinion of the International Searching Authority corresponding to International Patent Application No. PCT/US2015/055251 (13 pages) (dated Feb. 3, 2016).
(Continued)

*Primary Examiner* — Amanda K Hulbert
(74) *Attorney, Agent, or Firm* — Stanek Lemon Crouse & Meeks, PA

(57) ABSTRACT

Methods for combining anatomical data and physiological data on a single image are provided. The methods include obtaining an image, for example, a raw near-infrared (NIR) image or a visible image, of a sample. The image of the sample includes anatomical structure of the sample. A physiologic map of blood flow and perfusion of the sample is obtained. The anatomical structure of the image and the physiologic map of the sample are combined into a single
(Continued)

image of the sample. The single image of the sample displays anatomy and physiology of the sample in the single image in real time. Related systems and computer program products are also provided.

26 Claims, 12 Drawing Sheets

(51) Int. Cl.
  *G06T 5/50* (2006.01)
  *A61B 5/0275* (2006.01)
  *G06T 7/00* (2017.01)
  *A61B 90/00* (2016.01)

(52) U.S. Cl.
  CPC .......... *A61B 5/0086* (2013.01); *A61B 5/0261* (2013.01); *A61B 5/0275* (2013.01); *A61B 5/7225* (2013.01); *A61B 5/7425* (2013.01); *G06T 5/50* (2013.01); *G06T 7/0012* (2013.01); *A61B 5/0071* (2013.01); *A61B 2090/365* (2016.02); *A61B 2576/023* (2013.01); *G06T 2207/10024* (2013.01); *G06T 2207/20221* (2013.01); *G06T 2207/30104* (2013.01)

(58) Field of Classification Search
  CPC ..... A61B 5/0275; A61B 5/489; A61B 5/7225; A61B 5/7425; A61B 2090/365; A61B 2576/023; G06T 5/50; G06T 7/0012; G06T 2207/10024; G06T 2207/20221; G06T 2207/30104
  USPC ........................................................ 600/431
  See application file for complete search history.

(56) References Cited

U.S. PATENT DOCUMENTS

| | | | |
|---|---|---|---|
| 5,074,307 A | 12/1991 | Aizu et al. |
| 5,129,400 A | 7/1992 | Makino et al. |
| 5,161,531 A | 11/1992 | Parsons et al. |
| 5,240,006 A | 8/1993 | Fujii et al. |
| 5,291,885 A | 3/1994 | Taniji et al. |
| 5,291,886 A | 3/1994 | Katayama et al. |
| 5,490,505 A | 2/1996 | Diab et al. |
| 5,588,436 A | 12/1996 | Narayanan et al. |
| 5,692,510 A | 12/1997 | Gordon et al. |
| 5,860,922 A | 1/1999 | Gordon et al. |
| 6,045,511 A | 4/2000 | Ott et al. |
| 6,263,227 B1 * | 7/2001 | Boggett ............... A61B 5/0261 356/39 |
| 6,323,880 B1 * | 11/2001 | Yamada ............... G09G 3/2029 345/60 |
| 6,537,223 B1 | 3/2003 | Kristiansen |
| 6,587,701 B1 | 7/2003 | Stranc et al. |
| 6,631,286 B2 | 10/2003 | Pfeiffer et al. |
| 6,671,540 B1 | 12/2003 | Hochman |
| 6,766,188 B2 | 7/2004 | Soller |
| 6,915,154 B1 | 7/2005 | Docherty et al. |
| 6,944,494 B2 | 9/2005 | Forrester et al. |
| 6,974,416 B2 | 12/2005 | Booker et al. |
| 7,031,504 B1 | 4/2006 | Argiro et al. |
| 7,096,058 B2 | 8/2006 | Miyahara et al. |
| 7,113,817 B1 | 9/2006 | Winchester, Jr. et al. |
| 7,200,431 B2 | 4/2007 | Franco et al. |
| 7,231,243 B2 | 6/2007 | Tearney et al. |
| 7,270,637 B2 | 9/2007 | Shin |
| 7,309,313 B2 | 12/2007 | Nakata et al. |
| 7,404,640 B2 | 7/2008 | Ferguson et al. |
| 7,468,039 B2 | 12/2008 | Lui |
| 7,496,395 B2 | 2/2009 | Serov et al. |
| 7,541,602 B2 | 6/2009 | Metzger et al. |
| 7,542,790 B2 | 6/2009 | Jensen et al. |
| 7,809,225 B2 | 10/2010 | Bouma et al. |
| 7,809,226 B2 | 10/2010 | Bouma et al. |
| 9,028,421 B2 | 5/2015 | Fujii et al. |
| 9,226,673 B2 | 1/2016 | Ferguson, Jr. et al. |
| 9,271,658 B2 | 3/2016 | Ferguson, Jr. et al. |
| 9,610,021 B2 | 4/2017 | Dvorsky |
| 2001/0035503 A1 | 11/2001 | Quistorff et al. |
| 2002/0016533 A1 | 2/2002 | Marchitto et al. |
| 2002/0173723 A1 | 11/2002 | Lewis et al. |
| 2003/0120156 A1 | 6/2003 | Forrester |
| 2003/0225328 A1 | 12/2003 | DeMeester et al. |
| 2003/0231511 A1 | 12/2003 | Thibault |
| 2004/0068164 A1 | 4/2004 | Diab et al. |
| 2005/0046969 A1 | 3/2005 | Beatson et al. |
| 2006/0058662 A1 | 3/2006 | Kobayashi et al. |
| 2006/0241460 A1 | 10/2006 | Kimura et al. |
| 2006/0291708 A1 | 12/2006 | Dehmeshki et al. |
| 2007/0008615 A1 | 1/2007 | Miyawaki et al. |
| 2007/0100245 A1 | 5/2007 | Kashima |
| 2007/0109784 A1 | 5/2007 | Kosnick et al. |
| 2007/0203413 A1 * | 8/2007 | Frangioni ............... A61B 5/415 600/478 |
| 2008/0025579 A1 | 1/2008 | Sidlauskas |
| 2008/0049268 A1 | 2/2008 | Hardy et al. |
| 2008/0071176 A1 | 3/2008 | Docherty et al. |
| 2008/0107361 A1 | 5/2008 | Asukai et al. |
| 2008/0132794 A1 | 6/2008 | Alfano et al. |
| 2008/0188726 A1 | 8/2008 | Presura et al. |
| 2008/0262359 A1 | 10/2008 | Tearney et al. |
| 2009/0041201 A1 | 2/2009 | Wang et al. |
| 2009/0054908 A1 | 2/2009 | Zand et al. |
| 2009/0118623 A1 | 5/2009 | Serov et al. |
| 2009/0177098 A1 | 7/2009 | Yakubo et al. |
| 2009/0209834 A1 | 8/2009 | Fine |
| 2009/0214098 A1 | 8/2009 | Hornegger et al. |
| 2009/0216098 A1 | 8/2009 | Stranc et al. |
| 2009/0275841 A1 | 11/2009 | Melendez |
| 2010/0056936 A1 | 3/2010 | Fujii et al. |
| 2010/0067767 A1 | 3/2010 | Arakita et al. |
| 2010/0069759 A1 | 3/2010 | Schuhrke et al. |
| 2010/0168585 A1 | 7/2010 | Fujii et al. |
| 2010/0172567 A1 | 7/2010 | Prokoski |
| 2010/0209002 A1 | 8/2010 | Thiel et al. |
| 2010/0284693 A1 | 11/2010 | Agmon et al. |
| 2010/0305454 A1 | 12/2010 | Dvorsky et al. |
| 2011/0013002 A1 | 1/2011 | Thompson et al. |
| 2011/0068007 A1 | 3/2011 | Pang et al. |
| 2011/0071382 A1 | 3/2011 | Miyazaki et al. |
| 2011/0137169 A1 | 6/2011 | Akaki et al. |
| 2011/0164035 A1 | 7/2011 | Liao et al. |
| 2011/0169978 A1 | 7/2011 | Lasser et al. |
| 2011/0176048 A1 | 7/2011 | Rockley |
| 2011/0319775 A1 | 12/2011 | Fujii et al. |
| 2012/0071769 A1 | 3/2012 | Dunn et al. |
| 2012/0078113 A1 | 3/2012 | Hitestone et al. |
| 2012/0095354 A1 | 4/2012 | Dunn et al. |
| 2012/0108956 A1 | 5/2012 | Warger, II et al. |
| 2012/0165627 A1 | 6/2012 | Yamamoto |
| 2012/0191005 A1 | 7/2012 | Sobol et al. |
| 2012/0277559 A1 | 11/2012 | Kohl-Bareis et al. |
| 2013/0204112 A1 | 8/2013 | White |
| 2013/0223705 A1 | 8/2013 | Ferguson, Jr. |
| 2013/0245456 A1 | 9/2013 | Ferguson, Jr. |
| 2013/0324866 A1 | 12/2013 | Gladshtein |
| 2013/0345560 A1 | 12/2013 | Ferguson, Jr. et al. |
| 2014/0003740 A1 | 1/2014 | Bone |
| 2014/0081133 A1 | 3/2014 | Nie |
| 2014/0161421 A1 | 6/2014 | Shoemaker et al. |
| 2014/0187966 A1 | 7/2014 | Theirman |
| 2014/0213861 A1 | 7/2014 | Van Leest |
| 2014/0276097 A1 | 9/2014 | Sharonov |
| 2014/0285702 A1 | 9/2014 | Higashiyama et al. |
| 2014/0293091 A1 | 10/2014 | Rhoads et al. |
| 2014/0340482 A1 | 11/2014 | Kanarowski |
| 2015/0077716 A1 | 3/2015 | Peng |
| 2015/0148623 A1 | 5/2015 | Benaron |
| 2015/0196257 A1 | 7/2015 | Yousefi |
| 2015/0342479 A1 | 12/2015 | Liu et al. |
| 2016/0198961 A1 | 7/2016 | Homyk et al. |
| 2016/0270672 A1 | 9/2016 | Chen et al. |

(56) References Cited

U.S. PATENT DOCUMENTS

| | | |
|---|---|---|
| 2016/0278718 A1 | 9/2016 | Fujii |
| 2016/0317041 A1 | 11/2016 | Porges et al. |
| 2016/0358332 A1 | 12/2016 | Watanabe |
| 2017/0017858 A1 | 1/2017 | Roh |
| 2017/0049377 A1 | 2/2017 | Littell |
| 2017/0059408 A1 | 3/2017 | Korner |
| 2017/0091962 A1 | 3/2017 | Hagiwara |
| 2017/0135555 A1 | 5/2017 | Yoshizaki |
| 2017/0270379 A1 | 9/2017 | Kasai et al. |
| 2017/0274205 A1 | 9/2017 | Chen et al. |
| 2018/0153422 A1 | 6/2018 | Watanabe |

FOREIGN PATENT DOCUMENTS

| | | |
|---|---|---|
| CN | 102770071 A | 11/2012 |
| CN | 103340601 A | 10/2013 |
| CN | 103417196 A | 12/2013 |
| EP | 2 524 650 A2 | 11/2012 |
| JP | 10-290791 | 11/1998 |
| JP | 2005-118325 | 5/2005 |
| JP | 2005-185834 | 7/2005 |
| JP | 2007-125144 A | 5/2007 |
| JP | 2008-139543 | 6/2008 |
| JP | 2011-249267 A | 12/2011 |
| JP | 2012-130629 | 7/2012 |
| JP | 2013-118978 A | 6/2013 |
| JP | 2014-000246 A | 1/2014 |
| JP | 2015-223463 | 12/2015 |
| WO | WO 96/12435 | 5/1996 |
| WO | 97/43950 | 11/1997 |
| WO | 98/44839 | 10/1998 |
| WO | WO 2006/021096 A1 | 3/2006 |
| WO | WO 2006/116672 A2 | 11/2006 |
| WO | WO 2009/127972 A2 | 10/2009 |
| WO | WO 2010/131550 A1 | 11/2010 |
| WO | WO 2012/096878 A2 | 7/2012 |
| WO | WO 2013/190391 A2 | 12/2013 |
| WO | WO 2014/006465 A1 | 1/2014 |
| WO | WO 2014/009859 A2 | 1/2014 |
| WO | WO 2016/153741 A1 | 9/2016 |

OTHER PUBLICATIONS

Extended European Search Report corresponding to related European Patent Application No. 15849925.1 (7 pages) (dated Jun. 6, 2018).

Aizu, Y et al. (1991) "Bio-Speckle Phenomena and Their Application to the Evaluation of Blood Flow" Optics and Laser Technology, vol. 23, No. 4, Aug. 1, 1991.

Brezinski, M. E., G. J. Tearney, et al. (1996). "Imaging of coronary artery microstructure (in vitro) with optical coherence tomography." American Journal of Cardiology 77 (1): 92-93.

Briers et al., (1995) "Quasi real-time digital version of single-exposure speckle photography for full-field monitoring of velocity or flow fields," Optics Communications 116: 36-42.

Briers, J. David, (2001) "Laser Doppler, speckle and related techniques for blood perfusion mapping and imaging," Physiol. Meas. 22: R35-R66.

Chen, Z. P., T. E. Milner, et al. (1997). "Noninvasive imaging of in vivo blood flow velocity using optical Doppler tomography." Optics Letters 22(14): 1119-1121.

Cheng et al., (2004) "Laser speckle imaging of blood flow in microcirculation," Phys. Med. Biol., 49: 1347-1357.

Choi et al., "Linear response range characterization and in vivo application of laser speckle imaging of blood flow dynamics," Journal of Biomedical Optics, Jul./Aug. 2006, 11(4): 041129.

Cioffi, G. A. (2001). "Three common assumptions about ocular blood flow and glaucoma." Survey of Ophthalmology 45: S325-S331.

Draijer, Matthijs J., "High Speed Perfusion Imaging Based on Laser Speckle Fluctuations," Printed by Ridderprint, Ridderkerk, The Netherlands 2010, 145 pages.

Draijer et al., "Twente Optical Perfusion Camera: system overview and performance for video rate laser Doppler perfusion imaging," Optics Express, Mar. 2, 2009, 17(5): 3211-3225.

Duncan et al., "Can laser speckle flowmetry be made a quantitative tool?," J. Opt. Soc. Am. A, Aug. 2008, 24(8): 2088-2094.

Dunn et al. "Dynamic imaging of cerebral blood flow using laser speckle", J. of Cerebral Blood Flow and Metabolism 21, 195-201 (2001).

Dunn et al., (2011) A Transmissive Laser Speckle Imaging Technique for Measuring Deep Tissue Blood Flow: An Example Application in Finger Joints, Lasers in Surgery and Medicine, 43: 21-28.

Eun, H. C. (1995). "Evaluation of skin blood flow by laser Doppler flowmetry. [Review] [151 refs]." Clinics in Dermatology 13(4): 337-47.

Fercher et al., "Flow Visualization by Means of Single—Exposure Speckle Photography," Optics Communications, Jun. 1, 1981, 37(5): 326-330.

Gandjbakhche, A. H., P. Mills, et al. (1994). "Light-Scattering Technique for the Study of Orientation and Deformation of Red-Blood-Cells in a Concentrated Suspension." Applied Optics 33(6): 1070-1078.

Izatt, J. A., M. D. Kulkarni, et al. (1996). "Optical coherence tomography and microscopy in gastrointestinal tissues." IEEE Journal of Selected Topics in Quantum Electronics 2(4): 1017.

Jang, I. K., G. J. Tearney, et al. (2001). "Visualization of Tissue Prolapse Between Coronary Stent Struts by Optical Coherence Tomography: Comparison With Intravascular Ultrasound." Images in Cardiovascular Medicine, American Heart Association, http://circ.ahajournals.org/content, p. 2754.

Konishi and Fujii "Real-time visualization of retinal microcirculation by laser flowgraphy", Opt. Eng. 34, 753-757 (1995).

Kruijt et al., (2006), "Laser speckle imaging of dynamic changes in flow during photodynamic therapy," Lasers Med Sci, 21: 208-212.

Leitgeb, R. A., L. Schmetterer, et al. (2003). "Real-time assessment of retinal blood flow with ultrafast acquisition by color Doppler Fourier domain optical coherence tomography." Optics Express 11(23): 3116-3121.

Li et al., "Imaging cerebral blood flow through the intact rate skull with temporal laser speckle imaging," Optics Letters, Jun. 15, 2006, 31(12): 1824-1826.

Matsievskii, D.D., (2004) "Blood Flow Measurements in Studies of Macro- and Microcirculation," Bulletin of Experimental Biology and Medicine, 6: 541-544.

Nadkarni, Seemantini K. et al (2005) "Characterization of Atherosclerotic Plaques by Laser Speckle Imaging" Circulation vol. 112, pp. 885-892.

Nelson, J. S., K. M. Kelly, et al. (2001). "Imaging blood flow in human port-wine stain in situ and in real time using optical Doppler tomography." Archives of Dermatology 137(6): 741-744.

Ohtsubo et al., (1976) "Velocity measurement of a diffuse object by using time-varying speckles," Optical and Quantum Electronics, 8: 523-529.

Oshima, M., R. Torii, et al. (2001). "Finite element simulation of blood flow in the cerebral artery." Computer Methods in Applied Mechanics and Engineering 191 (6-7): 661-671.

Parthasarathy et al., "Laser speckle contrast imaging of cerebral blood flow in humans during neurosurgery: a pilot clinical study," Journal of Biomedical Optics, 15(6) Nov./Dec. 2010, pp. 066030-1 to 066030-8.

Rege et al., "Multiexposure laser speckle contrast imaging of the angiogenic microenvironment," Journal of Biomedical Optics, 16(5), May 2011, pp. 056006-1 to 056006-10.

Ren, Hongwu et al., "Phase-Resolved Functional Optical Coherence Tomography: Simultaneous Imaging of in Situ Tissue Structure, Blood Flow Velocity, Standard Deviation, Birefringence, and Stokes Vectors in Human Skin," Optics Letters, vol. 27, No. 19, Oct. 1, 2002, pp. 1702-1704.

Richards G.J. et al. (1997) "Laser Speckle Contrast Analysis (LASCA): A Technique for Measuring Capillary Blood Flow Using the First Order Statistics of Laser Speckle Patterns" Apr. 2, 1997.

Ruth, B. "blood flow determination by the laser speckle method", Int J Microcirc: Clin Exp, 1990, 9:21-45.

(56) References Cited

OTHER PUBLICATIONS

Ruth, et al., (1993) "Noncontact Determination of Skin Blood Flow Using the Laser Speckle Method: Application to Patients with Peripheral Arterial Occlusive Disease (PAOD) and to Type-I Diabetes," Lasers in Surgery and Medicine 13: 179-188.
Subhash, Hrebesh M., "Biophotonics Modalities for High-Resolution Imaging of Microcirculatory Tissue Beds Using Endogenous Contrast: A Review of Present Scenario and Prospects," International Journal of Optics, vol. 2011, Article ID 293684, 20 pages.
Tearney et al., "Atherosclerotic plaque characterization by spatial and temporal speckle pattern analysis", CLEO 2001, vol. 56, pp. 307-307.
Wang, X. J., T. E. Milner, et al. (1997). "Measurement of fluid-flow-velocity profile in turbid media by the use of optical Doppler tomography." Applied Optics 36(1): 144-149.
Wardell et al., "ECG-Triggering of the Laser Doppler Perfusion Imaging Signal," Proceedings of the $20^{th}$ Annual International Conference of the IEEE Engineering in Medicine and Biology Socieity, vol. 20, No. 4, 1998, pp. 1879-1880.
Weber et al., (2004) "Optical imaging of the spatiotemporal dynamics of cerebral blood flow and oxidative metabolism in the rat barrel cortex," European Journal of Neuroscience, 20: 2664-2670.
White, Brian R. et al., "In Vivo Dynamic Human Retinal Blood Flow Imaging Using Ultra-High-Speed Spectral Domain Optical Doppler Tomography," Optics Express, Dec. 15, 2003, 11(25): 3490-3497.
Wussling et al., "Laser diffraction and speckling studies in skeletal and heart muscle", Biomed, Biochem, Acta, 1986, 45(1/2):S 23-S 27.
Yazdanfar et al., "In Vivo imaging in blood flow in human retinal vessels using color Doppler optical coherence tomography", SPIE, 1999 vol. 3598, pp. 177-184.
Yazdanfar, S., A. M. Rollins, et al. (2000). "Imaging and velocimetry of human retinal circulation with color Doppler optical coherence tomography." Optics Letters, vol. 25, No. 19, Oct. 1, 2000, pp. 1448-1450.
Yazdanfar, S., A. M. Rollins, et al. (2003). "In vivo imaging of human retinal flow dynamics by color Doppler optical coherence tomography." Archives of Ophthalmology 121(2): 235-239.
Zakharov et al., "Dynamic laser speckle imaging of cerebral blood flow," Optics Express, vol. 17, No. 16, Aug. 3, 2009, pp. 13904-13917.
Zakharov et al., "Quantitative modeling of laser speckle imaging," Optics Letters, Dec. 1, 2006; 31(23): 3465-3467.
Zhao, Y. H., Z. P. Chen, et al. (2000). "Doppler standard deviation imaging for clinical monitoring of in vivo human skin blood flow." Optics Letters 25(18): 1358-1360.
U.S. Appl. No. 15/054,830, Chen et al., filed Feb. 26, 2016.
U.S. Appl. No. 15/559,605, Peng et al., filed Sep. 19, 2017.
U.S. Appl. No. 15/559,646, Peng et al., filed Sep. 19, 2017.
U.S. Appl. No. 15/688,472, Chen et al., filed Aug. 28, 2017.
Furstenberg et al. "Laser speckle reduction techniques for mid-infrared microscopy and stand-off spectroscopy" *Proceedings of SPIE* 10210:1021004-1-8 (2017).
Redding et al. "Speckle-free laser imaging using random laser illumination" *Nature Photonics* 6:355-359 (2012).
Ren et al. "A simultaneous multimodal imaging system for tissue functional parameters" *Proceedings of SPIE* 8937:893706-1-12 (2014).
Zhang et al. "Multimodal imaging of ischemic wounds" *Proceedings of SPIE* 8553:85531G-1-8 (2012).
LeSniok et al., "New Generation Optical Wound Monitoring Device," CW Optics, Inc., 2008 Mid-Atlantic Bio Conference, Chantilly, Virginia, USA, Oct. 24, 2018, 1 page.
Gioux et al., "Motion-gated acquisition for in vivo optical imaging," Journal of Biomedical Optics, Nov./Dec. 2009, vol. 14(6), pp. 064038-1 through 064038-8.
First Office Action, Chinese Patent Application No. 201580066744. 6, dated Oct. 9, 2019, 23 pages.
Decision of Refusal, Japanese Patent Application No. 2017-519928, dated Jan. 7, 2020, 5 pages.
Nakamura et al., "'Applying Hyper Eye Medical System; HEMS to abdominal surgery," Progress in Medicine, Mar. 10, 2011, vol. 31, No. 3, 806-809.
Notification of Reason(s) for Refusal, JP 2017-519923, dated Mar. 10, 2020. 7 pages.
Notification of Reason(s) for Refusal, JP 2017-568002, dated Mar. 31, 2020, 6 pages.

* cited by examiner

Fig. 10A
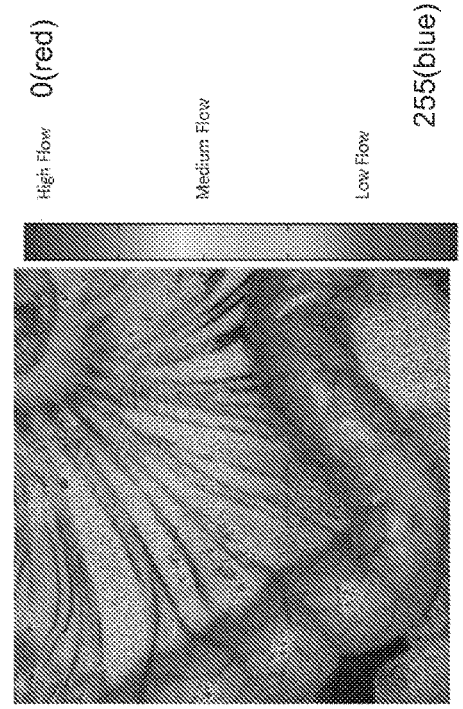
Fig. 10B
Fig. 10D
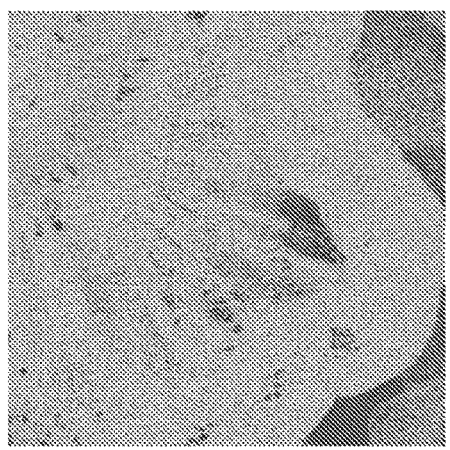
Fig. 10C

METHODS, SYSTEMS AND COMPUTER PROGRAM PRODUCTS FOR VISUALIZING ANATOMICAL STRUCTURES AND BLOOD FLOW AND PERFUSION PHYSIOLOGY USING IMAGING TECHNIQUES

CLAIM OF PRIORITY

The present application claims priority from U.S. Provisional Application Nos. 62/063,673, filed Oct. 14, 2014 and 62/136,010, filed Mar. 20, 2015, the disclosures of which are hereby incorporated herein by reference as if set forth in their entirety.

RESERVATION OF COPYRIGHT

A portion of the disclosure of this patent document contains material which is subject to copyright protection. The copyright owner, East Carolina University of Greenville, N.C., has no objection to the reproduction by anyone of the patent document or the patent disclosure, as it appears in the Patent and Trademark Office patent file or records, but otherwise reserves all copyright rights whatsoever.

FIELD

The inventive concept relates generally to visualization of organs and/or tissue and, more particularly, to visualization of anatomical structures, blood flow and perfusion.

BACKGROUND

Visible light imaging lends itself well to detailed anatomic visualization of a surface of organs and/or tissue for medical purposes. However, visible light imaging is not as useful for real-time imaging of physiology, particularly the physiology and pathophysiology of blood flow and perfusion. Near Infra-Red (NIR) imaging, on the other hand, can be used to visualize the surface of anatomic structures of target organs and/or tissue, but is substantially inferior to visible light anatomic imaging. Improved techniques for visualization of the organs and/or tissues are desired.

SUMMARY

Some embodiments of the inventive concept provide methods for combining anatomical data and physiological data on a single image, the methods including obtaining an image of a sample, the image of the sample including anatomical structure of the sample; obtaining a physiologic map of blood flow and perfusion of the sample; and combining the anatomical structure of the image and the physiologic map of the sample into a single image of the sample. The single image of the sample displays anatomy and physiology of the sample in the single image in real time. At least one of the obtaining an image, obtaining a physiologic map and combining is performed by at least one processor.

In further embodiments, obtaining may include obtaining at least one of a raw near-infrared (NIR) image having a wavelength of from about 780 nm to about 2500 nm and a visible light image having a wavelength of from about 400 nm to about 700 nm.

In still further embodiments, combining the anatomical structure of the image and the physiologic map of the sample into a single image may include adjusting one or more properties of the image and/or the physiologic map. The one or more properties may include at least one of colorization, transparency and a weight function. The physiologic map may illustrate one of blood flow and perfusion, flow distribution, velocity, and/or volume rate of blood flow (cc/min) quantification in primary vessels based on fluid dynamic modeling.

In some embodiments, combining may further include creating an 8 bit RGB color image represented by the following equation:

$$Img(i,j) = Img_A(i,j) \times RGB(i,j)$$

wherein $Img_A(i,j)$ is an 8 bit gray scale visible image of the target tissue/organ, wherein i and j are pixel indexes along horizontal and vertical directions, respectively, and $Img_A(i,j)$ for each color channel is adjusted separately to achieve a desired visualization effect.

In further embodiments, the sample may be one of tissue and an organ. Obtaining the image may include obtaining the image including anatomical structure of the vasculature of at least one of the tissue and the organ.

In still further embodiments, obtaining the image may be preceded by illuminating the sample with at least one light source. A portion of light may be reflected from the at least one light source to obtain the image and the physiologic map during a single data acquisition.

In some embodiments, obtaining a physiologic map of the sample may include obtaining one of a blood flow and perfusion physiologic map from one or more images using laser speckle imaging (LSI); a blood flow and perfusion physiologic map from one or more images using laser Doppler imaging (LDI); and a blood flow and perfusion angiography resemblance from a fluorescence image.

In further embodiments, the method may further include combining a plurality of images with a corresponding plurality of physiologic maps to provide a video displaying anatomy and physiology of the sample in real time.

Still further embodiments of the present inventive concept provide computer systems for combining anatomical data and physiological data on a single image, the system comprising includes a processor; and a memory coupled to the processor and comprising computer readable program code that when executed by the processor causes the processor to perform operations including obtaining an image of a sample, the image of the sample including anatomical structure of the sample; obtaining a physiologic map of blood flow and perfusion of the sample; and combining the anatomical structure of the image and the physiologic map of the sample into a single image of the sample. The single image of the sample displays anatomy and physiology of the sample in the single image in real time.

Some embodiments of the present inventive concept provide computer program products for combining anatomical data and physiological data on a single image, the computer program product including a non-transitory computer readable storage medium having computer readable program code embodied in the medium, the computer readable program code comprising computer readable program code to obtain a image of a sample, the image of the sample including anatomical structure of the sample; computer readable program code to obtain a physiologic map of blood flow and perfusion of the sample; and computer readable program code to combine the anatomical structure of the image and the physiologic map of the sample into a single image of the sample. The single image of the sample displays anatomy and physiology of the sample in the single image in real time.

BRIEF DESCRIPTION OF THE DRAWINGS

FIGS. 10A-10D are images illustrating a first approach to visualization of both anatomical structure and blood flow physiology of a small bowel in a pig study in accordance with some embodiments of the present inventive concept.

DETAILED DESCRIPTION OF SOME EMBODIMENTS

Figure 1:
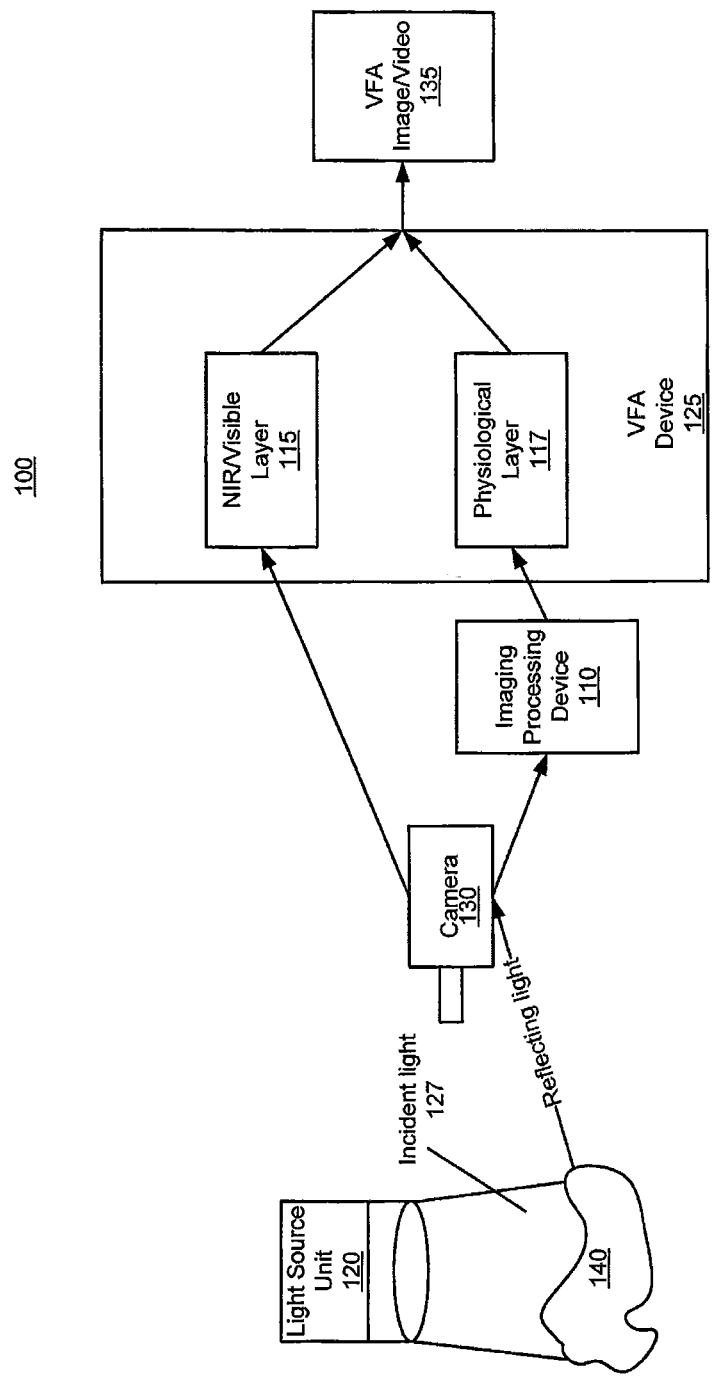
FIG. 1 is a block diagram of a system in accordance with some embodiments of the present inventive concept(s).

Specific example embodiments of the inventive concept now will be described with reference to the accompanying drawings. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. In the drawings, like numbers refer to like elements. It will be understood that when an element is referred to as being "connected" or "coupled" to another element, it can be directly connected or coupled to the other element or intervening elements may be present. As used herein the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and the relevant art and will not be interpreted in an idealized or overly formal sense unless expressly so defined herein.

As discussed above, both visible light imaging and near-infrared (NIR) imaging fall short in one or more areas of visualization, either anatomical or blood flow/perfusion. Accordingly, some embodiments of the present inventive concept combine visualization of anatomic structures with physiologic functionality derived from image data, for example, raw image data from the NIR spectrum of any open tissue/organ. In particular, some embodiments of the inventive concept combine an anatomical image obtained using NIR imaging, visible light imaging and the like and structural details related to blood flow/perfusion to provide a new image/video for presentation in real-time. The blood flow/perfusion data may be provided by, for example, Laser Speckle or Laser Doppler Imaging technology (LDI) or, in some embodiments, fluorescence imaging. Details of provision of the blood flow/perfusion data using Laser Speckle Imaging (LSI) are discussed in, for example, commonly assigned U.S. Patent Publication Nos. 2013/0223705 and 2013/0245456, the contents of which are hereby incorporated herein by reference as if set forth in their entirety. It will be understood that embodiments of the present inventive concept are not limited to LSI, LDI and/or fluorescence imaging, any image form that will represent blood flow and perfusion physiology may be used. In particular, the blood/flow and perfusion data may be provided by any effective method that lends itself to embodiments discussed herein without departing from the scope of the present inventive concept.

Some embodiments of the present inventive concept provide a new image/video visualization for presentation and real-time evaluation and assessment of an anatomical-physiological result. In other words, the new image provides both a usable anatomic image provided by, for example, NIR or visible light imaging, and blood/flow and perfusion information on a same image that can be manipulated in real-time. Thus, the new visualization, referred to hereinafter as a Velocity-Flow-Anatomy (VFA) image or video, contains information of both anatomic structure and blood flow and perfusion physiology simultaneously in real time.

The VFA image/video in accordance with some embodiments of the present inventive concept combines (1) highly specific anatomic detail with (2) underlying physiologic processes sufficient to make real-time medical decisions. An NIR/visible light image is used as one layer of the final visualization (VFA image), which reveals anatomical structure of the targeting tissue/organ surface and vasculature. The physiologic map of blood flow and perfusion quantified by, for example, LSI, LDI and fluorescence technology, is used as another layer of the final VFA visualization. The physiologic map provides functionality and physiology of the targeted tissue/organ vasculature. As will be understood herein, the term "physiologic map" refers to maps generated by different types of imaging, for example, LSI and LDI may generate a "velocity map," but the term "physiologic map" may generally refer to a map resulting from the use of any imaging technology. For example, a physiologic map may illustrate one of blood flow and perfusion, flow distribution, velocity, and/or volume rate of blood flow (cc/min) quantification in primary vessels based on fluid dynamic modeling and/or any the combination thereof without departing from the scope of the present inventive concept.

Both aspects of normal physiology of blood flow and perfusion and pathophysiological manifestations of abnormalities of blood flow and perfusion in tissues/organs may be provided. Some embodiments of the inventive concept provide software algorithms configured to adjust multiple aspects of each of the layers, for example, the colorization and transparency of the layers. In some embodiments, each of the layers may be derived from a same single video acquisition of raw NIR data/visible light image.

Some embodiments of the present inventive concept may provide distinct advantages over conventional visualization methods. For example, embodiments of the present inventive concept may provide substantially improved anatomic fidelity of the NIR image/visible light image. Furthermore, the anatomy layer may provide an important context for velocity imaging. The improved anatomic fidelity in turn improves the velocity fidelity, the velocity data interpretation, the timing of the interpretation, and the understanding of the interpretation; all of which make the interpretation of the VFA image/video result more intuitive. The anatomic fidelity allows for simultaneous, real-time assessment of multiple levels of analysis, such as target epicardial coronary arteries (flow) and surrounding myocardial tissue (perfusion). Finally, the combination of anatomy and physiology provided by embodiments of the inventive concept may be useful in convincing users, i.e., surgeons in surgical procedures, that the functional data is real and accurately represents the underlying physiology and/or pathophysiology. The VFA image/video combines and displays the unknown, i.e., quantification of perfusion, with the known, i.e., anatomy, where the anatomy component provides a useful frame of reference as will be discussed further herein with respect to FIGS. 1 through 11C.

Referring first to FIG. 1, a system for combining anatomic, and velocity information in a real time image/video in accordance with some embodiments of the present inventive concept will be discussed. It will be understood that some systems in accordance with embodiments of the present inventive concept may be non-invasive. As used herein, "non-invasive" refers to a system or method that does not require the subject to be injected with a dye, penetrated with an object or touched with an intrabody probe or probes. Thus, as used herein, the term non-invasive refers to a system or method that makes minimal contact with the subject. As used herein, "subject" refers to the person or thing being imaged. The subject can be any subject, including a veterinary, cadaver study or human subject. As used herein, "perfusion" refers to blood flow at the tissue perfusion distribution level detected with speckle imaging.

As illustrated in FIG. 1, the system 100 includes at least one light source unit 120, a camera 130, an image processing device 110 and a VFA device 125. Although the system of FIG. 1 is depicted as only including these elements, it will be understood that other elements may also be present in the system without departing from the scope of the present inventive concept. For example, some embodiments of the present inventive concept may include multiple light sources 120 without departing from the scope of the present inventive concept. The multiple light sources 120 may include light sources having different wavelengths, for example, near infra-red and visible light maybe provided by respective light/laser devices.

In particular, in some embodiments, the light source unit 120 may be, provided by, for example, one or more lasers or light emitting diode (LED) lights. In some embodiments, the light source 120 is an NIR light source having a wavelength of from about 780 nm to about 2500 nm. In some embodiments, the light source 120 may be a visible light source having a wavelength of from about 400 nm to about 780 nm.

In some embodiments, both a visible light source and a NIR light source may be used having the respective wavelength. Thus, some embodiments of the present inventive concept provide a system that uses two wavelengths of differential transmittance through a sample to apply LSI and/or LDI. For example, a first of the two wavelengths may be within the visible range that has zero or very shallow penetration, such as blue light 450-495 nm. This wavelength captures the anatomical structure of tissue/organ surface and serves as a position marker of the sample but not the subsurface movement of blood flow and perfusion. A second wavelength may be in the near Infra-Red (NIR) range, which has much deeper penetration. This wavelength reveals the underlying blood flow physiology and correlates both to the motion of the sample and also the movement of blood flow and perfusion. Using the imaging measurement of the visible light as a baseline, the true motion of blood flow and perfusion can be derived from the NIR imaging measurement without being affected by the motion artifact of the target. Furthermore, the anatomical structure information captured by visible light and the physiological characteristics measured by NIR light are combined. Details with respect to systems using two wavelengths are discussed in detail in U.S. Provisional Application No. 62/136,010, filed Mar. 20, 2015, the disclosure of which was incorporated herein by reference above. Although embodiments are discussed herein with respect to NIR raw images and visible light images, embodiments of the present inventive concept are not limited to this configuration. Any other image form that can adequately represent anatomy can be used without departing from the scope of the present inventive concept.

The light source 120 may be used to illuminate a region of interest 140 (hereinafter "tissue/organ"). As used herein, the "region of interest" refers to the region of the subject that is being imaged, for example, the principal vessels and tissue, organs, etc. When incident light 127, for example, NIR light or visible light, from the source 120 is directed to a living target (region of interest 140), such as a tissue/organ, part of the light will go through multiple scattering inside the target and eventually reflect back (Reflecting light) to the camera 130 as shown in FIG. 1.

The camera 130 is configured to collect the reflecting light and provide a visible light or NIR image (NIR/Visble Layer 115), each with different characteristics depending, for example, upon a depth of penetration of the illumination light determined by the wavelength energy. In some embodiments, the camera 130 is provided by Lumenera Lt225 NIR CMOS camera for single wavelength (Visible/NIR) image acquisition. For simultaneous multiple wavelength image acquisition applications, a customer designed beam splitting system may be located in front of the regular camera body.

The reflected NIR/Visible image 115 reveals an anatomical structure. In some embodiments, this anatomical structure may be multiple millimeters beneath the surface of the tissue/organ, depending on the penetration into the tissue, which is a function of wavelength and energy. The resulting unmodified image presentation (the raw NIR image of FIG. 4) is not as detailed as a visible light image of a similar structure (FIG. 3).

Figure 3:
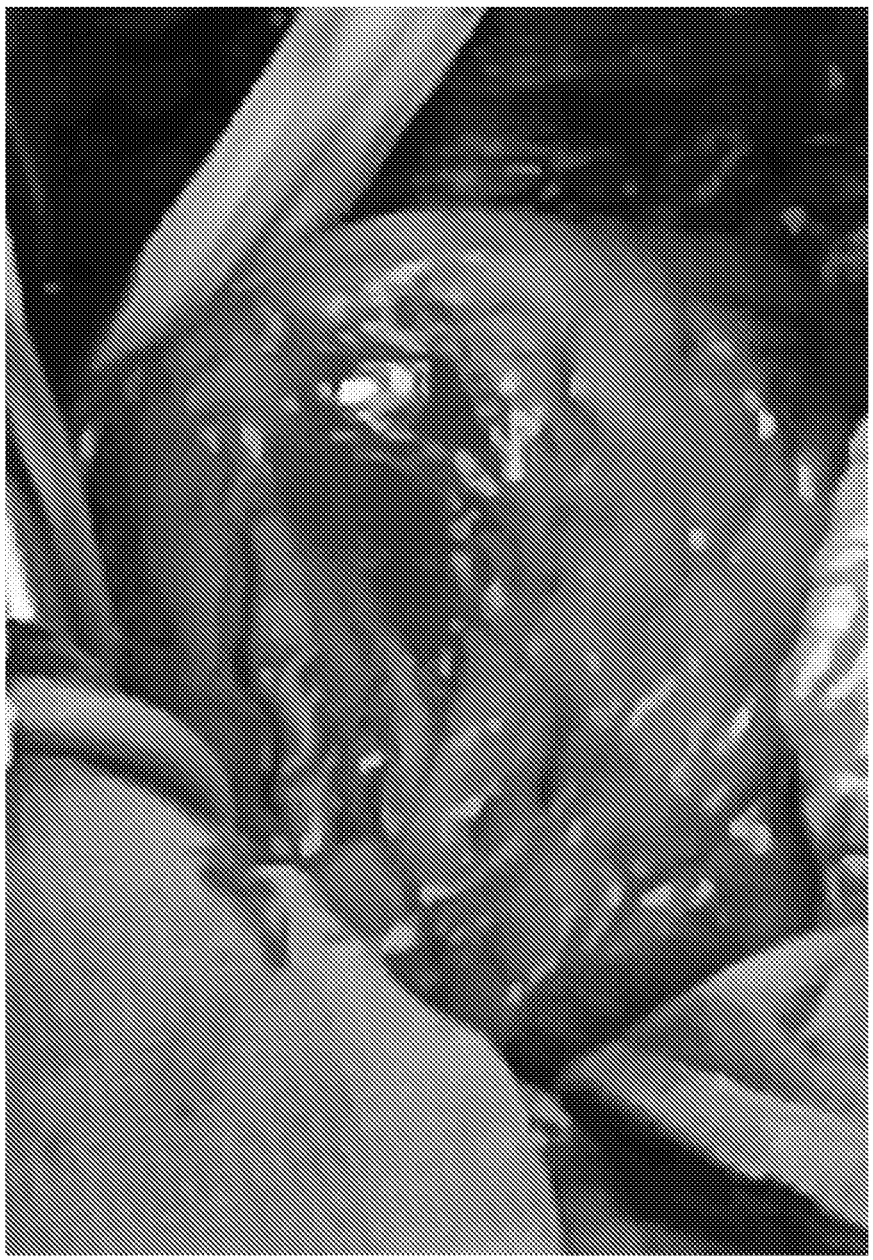
FIG. 3 is a visible light image of an anterior wall of a heart.
Figure 4:
FIG. 4 is a near-infrared (NIR) image of an anterior wall of a heart.
Figure 5:
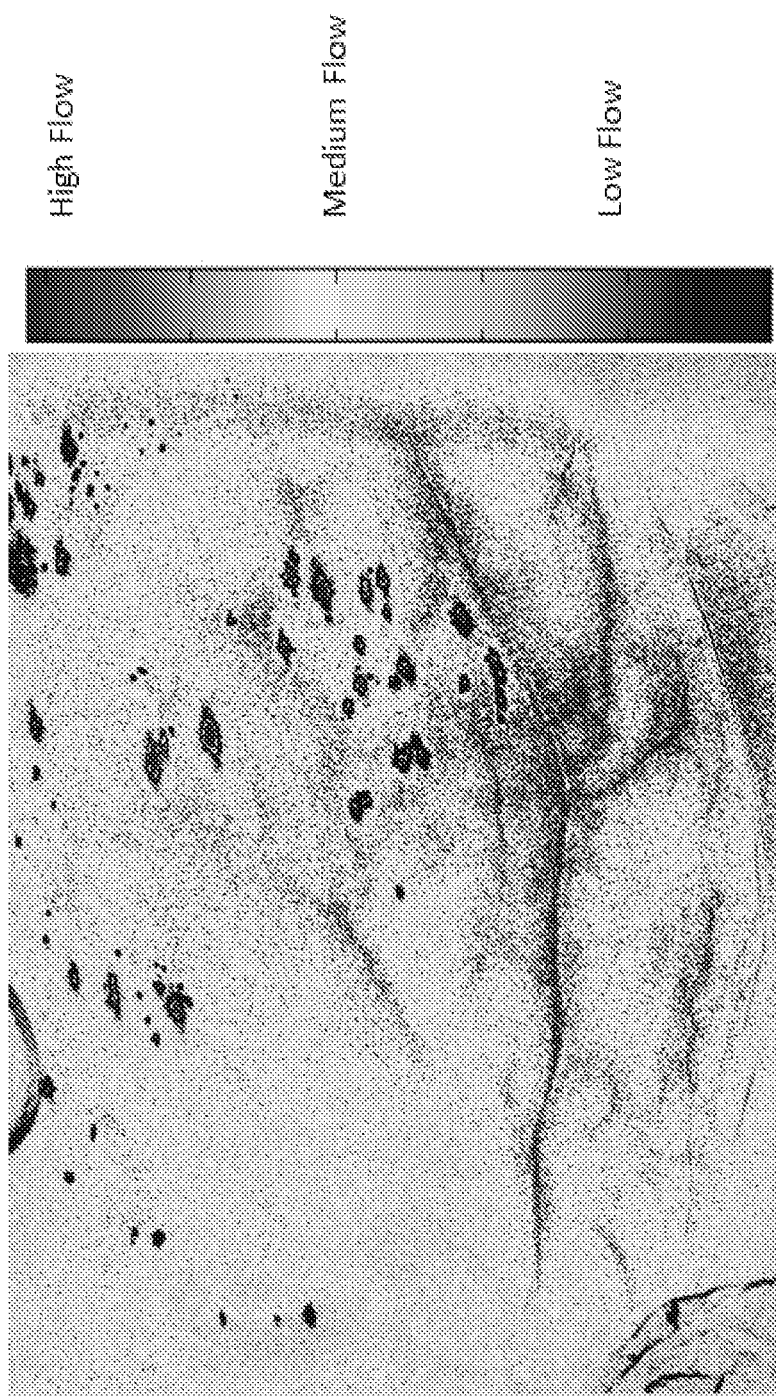
FIG. 5 is an image illustrating blood flow and perfusion on anterior wall of a human heart based on Laser Speckle Contrast imaging technology.

FIG. 3 is a visible light image of anterior wall of a heart and FIG. 4 is an NIR image of anterior wall of a heart, which reveals the anatomical structure of the coronary arteries. The differences between FIGS. 3 and 4 are based on both velocity differences, not just anatomic structures.

Moreover, since the NIR image of FIG. 4 is a 256-grey scale image, the anatomic differentiation achieved by color may be lost in the NIR raw image. The loss of fidelity has limited application of, for example, LSI and LDI in medicine to a great extent. Anatomy and anatomic structures are a fundamental reference construct in medicine, particularly in surgical and interventional procedures. Loss of the anatomic fidelity removes a key framework for understanding the physiologic and pathophysiologic blood flow and perfusion data, and for making the use of such an imaging technology more intuitive.

Accordingly, as illustrated in FIG. 1, embodiments of the present inventive concept provide a VFA device 125 that is configured to provide the VFA image/video 135. In particular, as illustrated in FIG. 1, the VFA device 125 is configured to combine the NIR/Visible anatomic image 115 with the blood flow and perfusion information 117 (physiological layer) provided by an image processing device 110, for example, LSI, LDI or fluorescence, to provide higher-fidelity anatomic details in combination with the physiologic map data on blood flow and perfusion for the components of that anatomic detail, i.e., flow in epicardial coronary arteries and perfusion in the surrounding myocardium. Thus, the VFA image/video 135 uniquely combines these two types of data. The new VFA image 135 in accordance with embodiments discussed herein displays the flow and perfusion velocity data provided by, for example, LSI, LDI or fluorescence, with anatomic fidelity that is better than the raw NIR/Visible image 115 (FIG. 4) and almost as detailed as the visible light image (FIG. 3).

The VFA image presentation of the LSI analysis creates a methodology for presenting the velocity data within a framework already known and understood by surgeons and medial imagers, thus making the interpretation of the novel flow and perfusion data more readily understandable and usable for decision-making. The anatomic detail provides the frame of reference to combine the known (anatomy) with the unknown or measured (flow and perfusion). The anatomic detail improves the accuracy of interpretation and understanding of the flow and perfusion data, in both physiologic and pathophysiologic circumstances. This is particularly true when the imaging technology is challenged to provide two different 'levels' of velocity (and flow) data, for example, when the epicardial surface of the heart is imaged to measure flow in the epicardial coronaries (level 1) and perfusion in the surrounding myocardium (level 2).

In some embodiments of the inventive concept, both the anatomic detail and the physiologic map analysis can be derived from a same single raw NIR image data/visible light image. Thus by combining these anatomic and analysis data, and using algorithms in accordance with embodiments of the present inventive concept to adjust, for example, the colorization, transparency, superposition and integration of the data, a new VFA analysis image 135 can be generated to contain both anatomical (vascular structure) and functional (blood flow and perfusion) information of the tissue/organ as illustrated in, for example, FIG. 6.

Figure 6:
FIG. 6 is an image in accordance with embodiments of the present inventive concept combining the images of FIGS. 3 and 4.

In particular, FIG. 6 illustrates the VFA image after processing in accordance with some embodiments of the present inventive concept. Thus, FIG. 6 illustrates the VFA image/video display of the combination of FIGS. 4 and 5. In some embodiments of the present inventive concept, the colorization, transparency and other features of each layer are adjusted, to optimally reveal both anatomy and functionality of the (coronary) arteries flow and surrounding tissue (myocardial) perfusion, simultaneously and in real-time.

Figure 7:
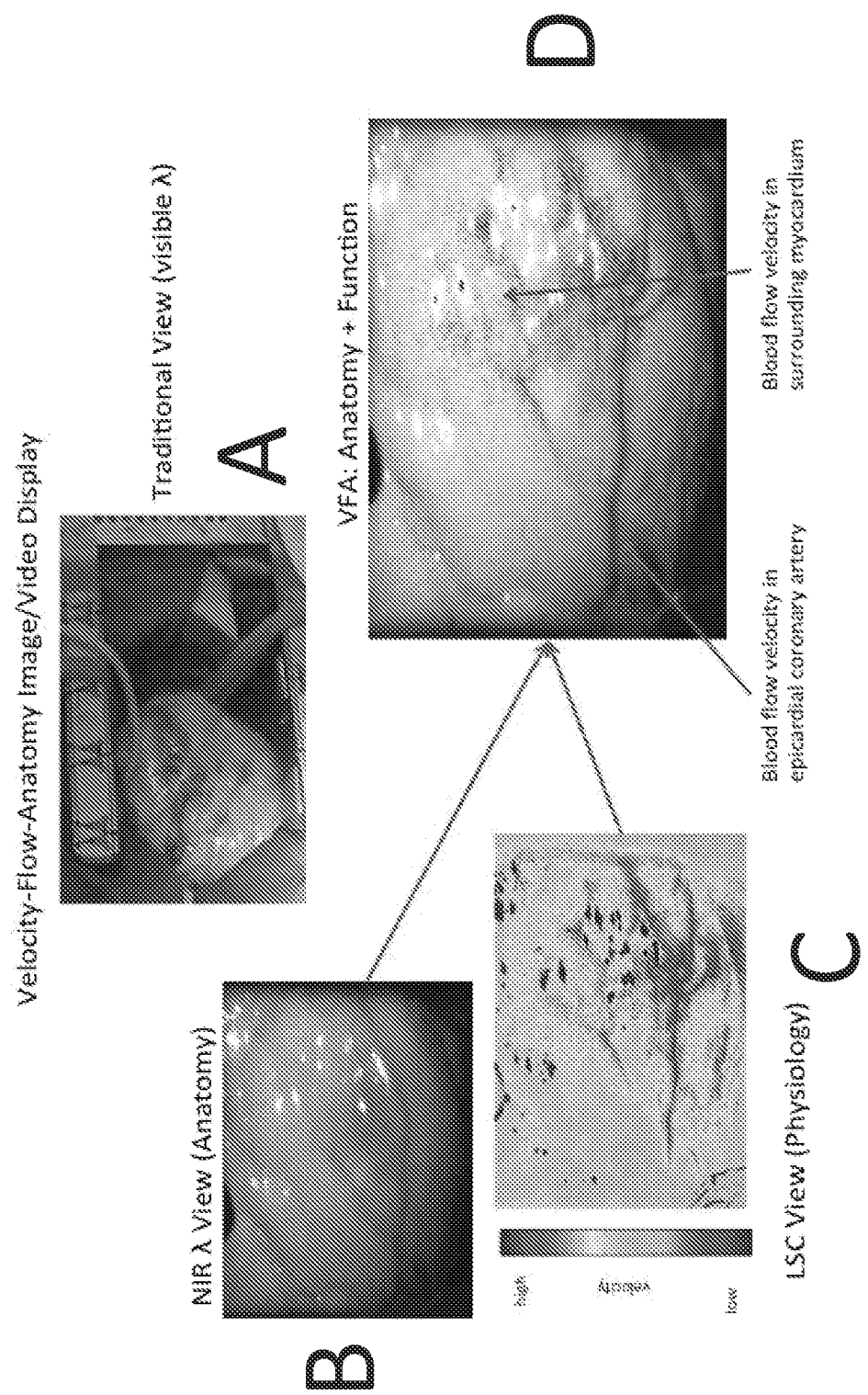
FIG. 7 is a series of images resulting in the combination image generated in accordance with some embodiments of the present inventive concept.

Referring now to FIG. 7, a VFA image/video in accordance with some embodiments of the present inventive concept will be discussed. FIG. 7A illustrates a conventional anatomy image of a heart provided with visible wavelength imaging. FIG. 7B illustrates an anatomy view generated with NIR imaging. FIG. 7C is a physiology image generated using LSI detailing the blood flow and perfusion on the sample. The VFA image in accordance with embodiments of the present inventive concept combines 7B and 7C to illustrate the anatomy of the sample as well as the physiology (blood flow and perfusion) as illustrated in FIG. 7D. The considerable value-added to this VFA analysis image approach in making this combined data more visually intuitive than either of the components (anatomy, velocity) and, thus, easier to quickly understand and interpret on the part of the provider/medical practitioner. This may directly translate to better healthcare delivered by practitioners with much more physiologic and pathophysiologic data than ever before at their disposal. Real-time data is readily acquired and then intuitively presented in the VFA image in accordance with embodiments of the inventive concept to allow for better decisions and better, safer surgical procedures.

It will be understood that although generation of a single VFA image has been discussed herein, embodiments of the present inventive concept are not limited to this configuration. For example, a series of VFA images may be generated and may be assembled into a VFA video image sequence without departing from the scope of the present inventive concept.

Embodiments of the present inventive concept may be applied to the determined acquisition of blood flow and perfusion data from any tissue and/or organ system where blood flow and perfusion are an important determinant for evaluation, measurement, clinical decision-making, therapeutic decision-making, product development using physiologic imaging data derived from this technique, or experimental investigation into the physiology and/or pathophysiology of blood flow and perfusion.

Figure 2A:
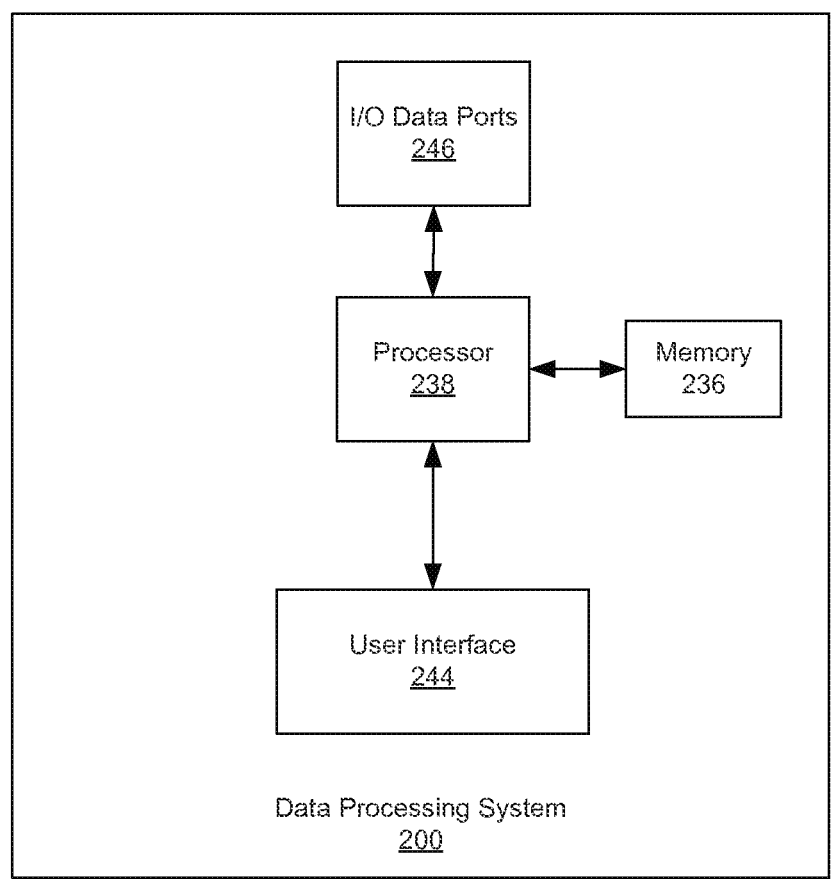
FIG. 2A is a block diagram of a data processing system according to embodiments of the present inventive concept(s).
Figure 2B:
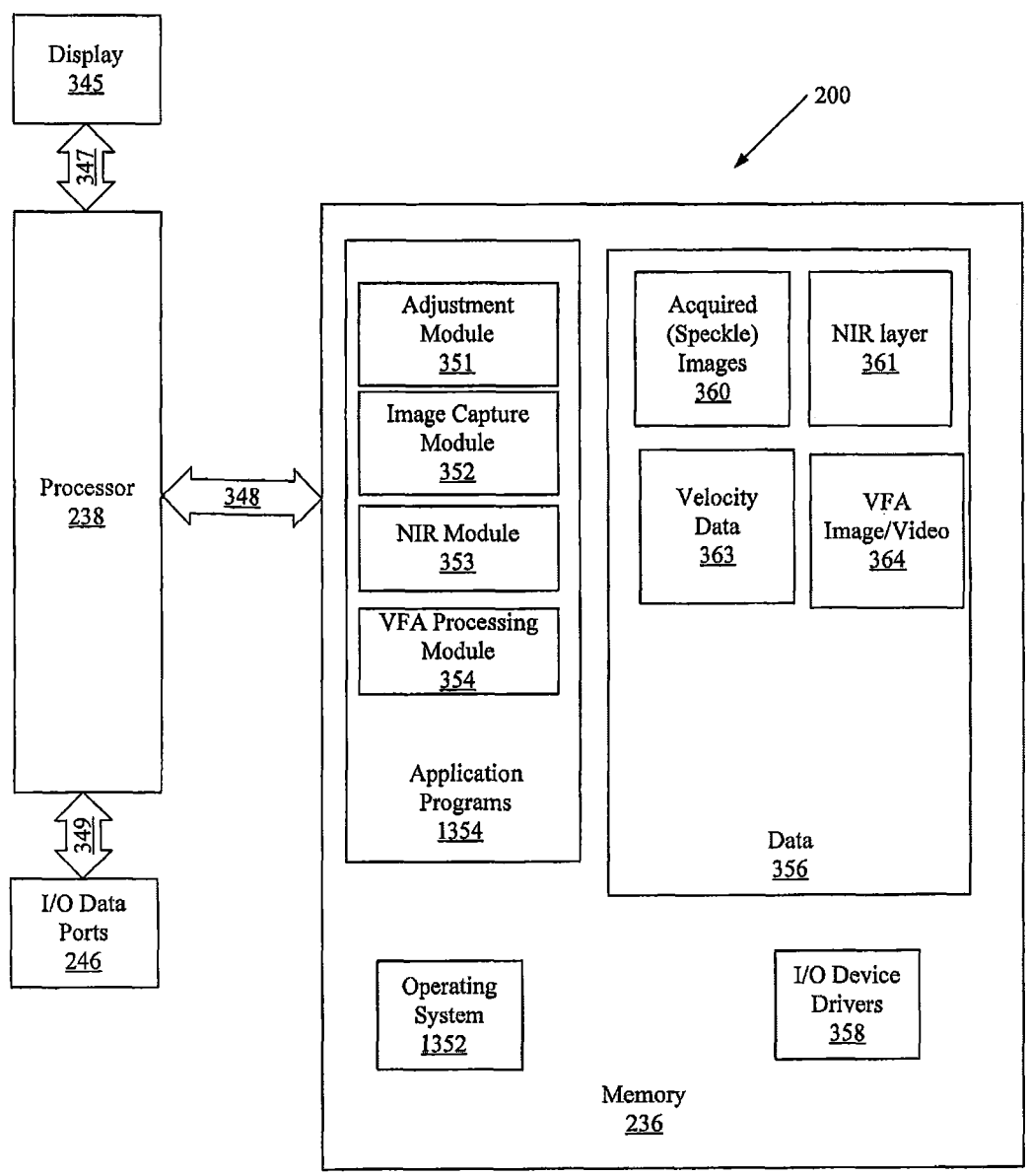
FIG. 2B is a more detailed block diagram of the data processing system illustrated in FIG. 2 in accordance with some embodiments of the present inventive concept(s).

Referring now to FIGS. 2A and 2B, a data processing system 200 that may be used in the system 100 illustrated in FIG. 1 in accordance with some embodiments of the inventive concept will be discussed. The data processing system 200 may be included in the VFA device 120, the camera 130 or split between various elements of the system 100 without departing from the scope of the present inventive concept. As illustrated in FIG. 2, an exemplary embodiment of a data processing system 200 suitable for use in the system 100 of FIG. 1 includes a user interface 244 such as a keyboard, keypad, touchpad or the like, I/O data ports 246 and a memory 236 that communicates with a processor 238. The I/O data ports 246 can be used to transfer information between the data processing system 200 and another computer system or a network. These components may be conventional components, such as those used in many conventional data processing systems, which may be configured to operate as described herein.

Referring now to FIG. 2B, a more detailed block diagram of the data processing system 200 in accordance with some embodiments of the present inventive concept will be discussed. The processor 238 communicates with a display 345 via and address/data bus 347, the memory 236 via an address/data bus 348 and the I/O data ports 246 via an address/date bus 349. The processor 238 can be any commercially available or custom microprocessor or ASICs. The memory 236 is representative of the overall hierarchy of memory devices containing the software and data used to implement the functionality of the data processing system 200. The memory 236 can include, but is not limited to, the following types of devices: cache, ROM, PROM, EPROM, EEPROM, flash memory, SRAM, and DRAM.

As shown in FIG. 2B, the memory 236 may include several categories of software and data used in the data processing system 200: an operating system 1352; application programs 1354; input/output (I/O) device drivers 358; and data 356. As will be appreciated by those of skill in the art, the operating system 1352 may be any operating system suitable for use with a data processing system, such as OS/2, AIX or zOS from International Business Machines Corporation, Armonk, N.Y., Windows95, Windows98, Windows2000, WindowsXP, or Vista from Microsoft Corporation, Redmond, Wash., Unix, Linux, LabView, or a real-time operating system such as QNX or VxWorks, or the like. The I/O device drivers 358 typically include software routines accessed through the operating system 1352 by the application programs 1354 to communicate with devices such as the I/O data port(s) 246 and certain memory 236 components. The application programs 1354 are illustrative of the programs that implement the various features of the data processing system 200 included a system in accordance with some embodiments of the present inventive concept and preferably include at least one application that supports operations according to some embodiments of the present inventive concept. Finally, the data 356 represents the static and dynamic data used by the application programs 1354, the operating system 1352, the I/O device drivers 358, and other software programs that may reside in the memory 236.

As illustrated in FIG. 2B, the data 356 according to some embodiments of the present inventive concept may include acquired raw images 360, anatomical layer images/data 361, calculated blood flow/perfusion rates (velocity data) 363, VFA images/videos 364 and volume rate of blood flow (cc/min) data 365. The volume rate of blood flow (cc/min) data 365 is directed to volume rate of blood flow (cc/min) quantification on primary vessel based on fluid dynamic modeling.

Although the data 356 illustrated in FIG. 2B includes five different files 360, 361, 363, 364 and 365 embodiments of the present inventive concept are not limited to this configuration. Two or more files may be combined to make a single file; a single file may be split into two or more files and the like without departing from the scope of the present inventive concept.

As further illustrated in FIG. 2B, the application programs 1354 may include an adjustment module 351, an image capture module 352, a NIR/Visible module 353 and a VFA processing module 354 in accordance with some embodiments of the inventive concept. While the present inventive concept is illustrated, for example, with reference to the adjustment module 351, the image capture module 352, the NIR/Visible module 353 and the VFA processing module 354 being application programs in FIG. 2B, as will be appreciated by those of skill in the art, other configurations may also be utilized while still benefiting from the teachings of the present inventive concept. For example, the adjustment module 351, the image capture module 352, the NIR/Visible module 353 and the VFA processing module 354 may also be incorporated into the operating system 1352 or other such logical division of the data processing system 300. Thus, the present inventive concept should not be construed as limited to the configuration of FIG. 2B, but is intended to encompass any configuration capable of carrying out the operations described herein.

Furthermore, while the adjustment module 351, the image capture module 352, the NIR/Visible module 353 and the VFA processing module 354 are illustrated in a single data processing system, as will be appreciated by those of skill in the art, such functionality may be distributed across one or more data processing systems. Thus, the present inventive concept should not be construed as limited to the configuration illustrated in FIGS. 2A and 2B, but may be provided by other arrangements and/or divisions of function between data processing systems.

As discussed above with respect to FIG. 1, a light source, for example, an NIR source and/or visible light source, may illuminate a sample of tissue/organ and light may be reflected into a camera. The NIR/Visible module 353 may provide an NIR image 361 from the reflected light and the image capture module 352 may provide an image (speckle image) 360 using, for example, LSI, LDI, or fluorescence. Blood flow and perfusion data may be calculated (velocity data). These images may be processed to provide velocity date 363 and at least one VFA image 364 in accordance with embodiments discussed herein. In particular, the data 356 may be used by the VFA processing module 354 to provide a combination of the NIR image 361 and the velocity data 363. As discussed above, color, transparency and the like of the NIR image 361 may be adjusted by the adjustment module 351 to provide a real time, usable image including both anatomical and physiological data.

In some embodiments, a solid color, for example, black, is used as the base at the bottom; a physiological image or its adjusted form is used as a layer on top of the base; an anatomical image or its adjusted form is used to modify the transparency of the physiological layer, so the anatomically less significant part (lower intensity in the anatomical image) will make the physiological image more transparent and, thus, less visible.

In further embodiments, a solid color, for example, black, is used as the base at the bottom; an anatomical image or its adjusted form is used as a layer on top of the base; and the physiological image or its adjusted form is used to modify the transparency of the anatomical layer, so the physiologically less significant part (lower value in the physiological image) will make the anatomical image more transparent and, thus, less visible.

Using the NIR wavelength, Laser Speckle Image and Laser Doppler technologies can quantify the speed of blood flow and perfusion and, thus, reveal the functionality of the vascular system. In many clinical situations, the novel opportunity to use real-time visualization of the combination of anatomic detail and the underlying physiologic processes within that anatomic detail will be transformational in current and future therapeutic strategies.

Figure 8:
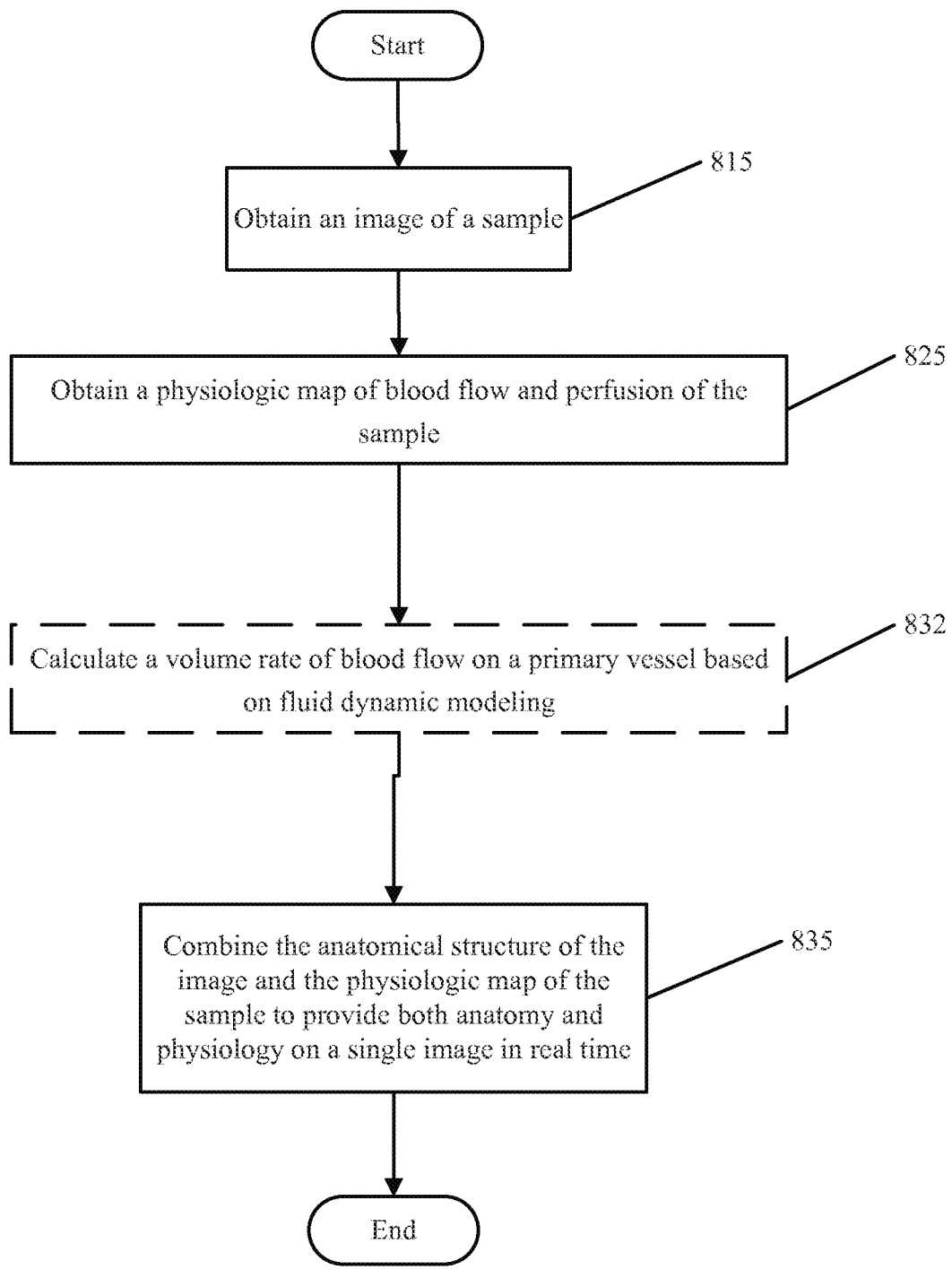
FIGS. 8 through 9 are flowcharts illustrating operations for combining images in accordance with various embodiments of the present inventive concept(s).

Operations in accordance with various embodiments of the inventive concept will now be discussed with respect to the flowcharts of FIGS. 8 and 9. Referring first to FIG. 8, operations for combining anatomical data and physiological data on a single image begin at block 815 by obtaining an image of a sample. The image may be, for example, a raw near-infrared (NIR) image of the sample having a wavelength of from about 780 nm to about 2500 nm and/or a visible light image of the sample having a wavelength of from about 400 nm to about 700 nm.

The image of the sample includes anatomical structure of the sample. The sample may be, for example, tissue and/or organs. A physiologic map of blood flow and perfusion of the sample is obtained (block 825). The physiologic map of the sample may be obtained using, for example, LSI, LDI or fluorescence. The anatomical structure of the image and the physiologic map of the sample are combined into a single image of the sample (block 835). The single image of the sample displays anatomy and physiology of the sample in the single image in real time. As further illustrated in FIG. 8, in some optional embodiments, a volume rate of blood flow (cc/min) may be calculated on a primary vessel based on fluid dynamic modeling (block 832).

In some embodiments, a plurality of images may be combined with a corresponding plurality of physiologic maps to provide a video displaying anatomy and physiology of the sample in real time.

In some embodiments, combining the anatomical structure of the image and the physiologic map of the sample into a single image includes adjusting one or more properties of the image and/or the physiologic map. The one or more properties may include at least one of colorization, transparency and a weight function.

Figure 9:
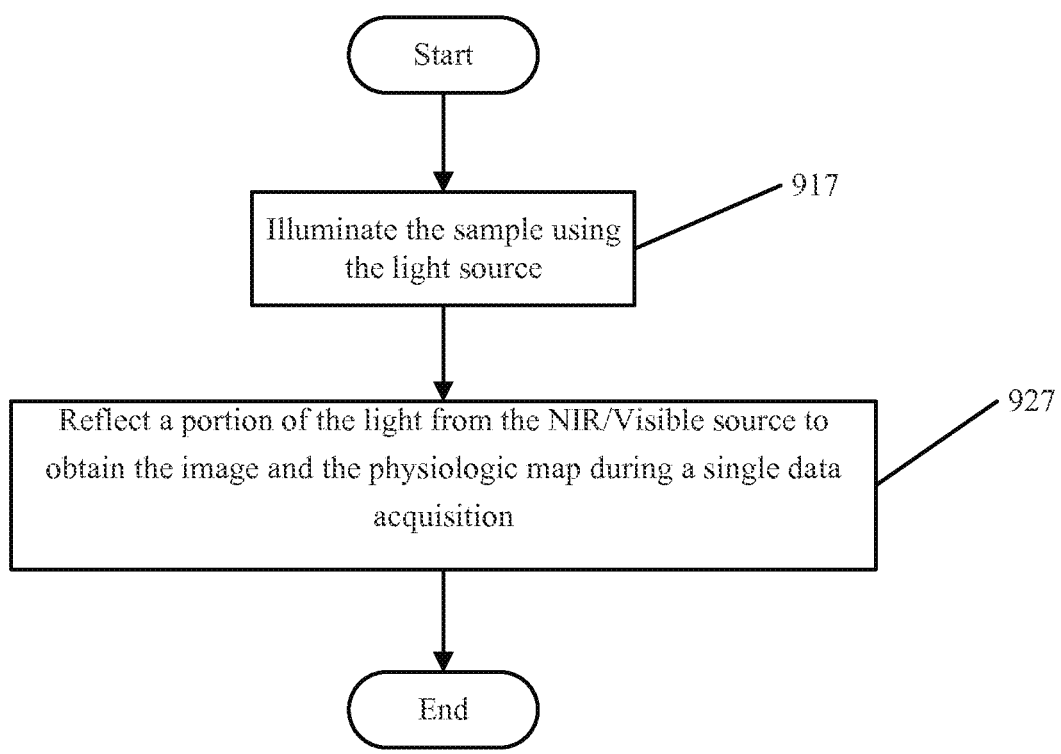

Referring now to FIG. 9, in some embodiments, operations for obtaining are preceded by illuminating the sample with a light source (block 917), for example, an NIR source and/or a visible light source. In these embodiments, a portion of light is reflected from the source to obtain the image and the physiologic map during a single data acquisition (block 927).

Further operations in accordance with embodiments discussed herein will now be discussed with respect to the images illustrated in FIGS. 10A-11C. It will be understood that the visualization of both anatomical structure and blood flow physiology of the tissue and organs as discussed herein can be achieved by various approaches. Two different approaches will now be discussed herein with respect to FIGS. 10A-11C.

Referring first to FIGS. 10A-10D, a first approach using a dual layers design similar to operations discussed above will be discussed. FIGS. 10A and 10B illustrate an anatomical layer, which is a raw (original) image frame of one wavelength illumination (visible and/or near infra-red). $Img_A(i,j)$ are 8 bit gray scale visible images of the target tissue/organ and i and j are the pixel indexes along horizontal and vertical direction. The brightness, contrast and gamma value of this image might be adjusted to achieve better visualization effect.

FIG. 10C illustrates the physiological layer, which is a processed image based on one or more raw image frames of near infra-red light to reflect 2D speed distribution of blood flow and perfusion of the imaged tissue/organ using, for example, LSI or LDI technology. $Img_p(i,j)$ is an 8 bit indexed color image (shown in black and white) with its numerical values mapped to a predefined color map. Usually, the color ranges from blue to red (0 to 255) with blue representing no/minimum flow speed and red representing the highest flow speed that the system can detect.

Finally, FIG. 10D illustrates a combination of FIGS. 10A-10C. Using conventional methods that overlap the anatomical layer or parts of the anatomical layer over the physiological layer will cause the bottom layer to be invisible (covered) or partially invisible (partially covered). Similarly, using conventional methods that overlap the physiological layer or parts of the physiological layer over the anatomical layer will cause the bottom layer to be invisible (covered) or partially invisible (partially covered). Thus, embodiments of the present inventive concept provide a transparency map/matrix that is applied to increase the visibility of both the anatomical and physiological layers. The transparency map may be represented by the following equation:

$$T(i,j) = \left( \frac{Img(i,j) - \text{Min}(Img(i,j))}{\text{Max}(Img(i,j)) - \text{Min}(Img(i,j))} \right)^x \qquad \text{Eqn. (1)}$$

where Img is a raw (original) image frame of visible or near infra-red light (10A or 10B) and x is an adjustable parameter greater than zero (>0) and less and or equal to two (<=2). In other words, each pixel value in T(i,j) is between 0 and 1 with 0 representing no transparency and 1 representing 100% transparency. Parameter x controls the contrast of the transparency map and if x>1, transparency has a larger dynamic range and if x<1, the transparency has a smaller dynamic range.

Figure 11B:
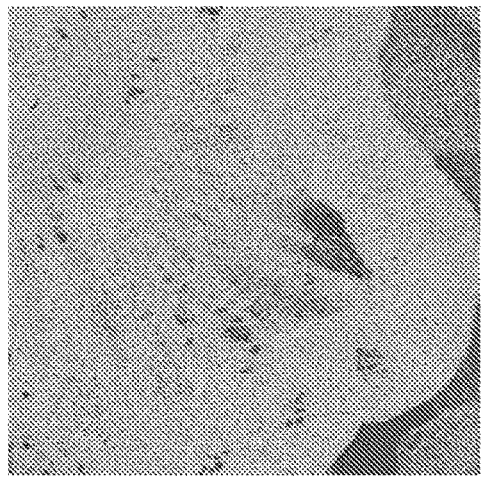
FIGS. 11A-11C are images illustrating a second approach to visualization of both anatomical structure and blood flow physiology of a small bowel of a pig study in accordance with some embodiments of the present inventive concept.
Figure 11C:
Figure 11A:
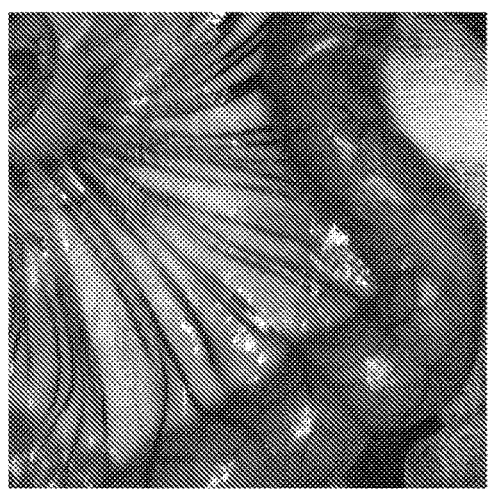

Referring now to FIGS. 11A-11C, a second approach for visualization of both anatomical structure and blood flow physiology of the tissue and organs using color and brightness design will be discussed. Referring first to FIG. 11A, an anatomical layer is illustrates that is represented by image brightness. A raw (original) image frame of one wavelength illumination (visible and/or near infra-red). $Img_A(i,j)$ is a 8 bit gray scale visible image of the target tissue/organ and i and j are the pixel indexes along horizontal and vertical direction. The brightness, contrast and gamma value of this image might be adjusted to achieve better visualization effect.

FIG. 11B illustrates the physiological layer as a colored image (shown in black and white), which is a processed image based on one or more raw image frames of near infra-red light to reflect 2D speed distribution of blood flow and perfusion of the imaged tissue/organ using, for example, LSI or LDI technology. First, an 8 bit indexed color image is generated with its numerical values mapped to a predefined color map. Usually, the color ranges from blue to red (0 to 255) with blue representing no/minimum flow speed and red representing the highest flow speed that the system can detect as discussed above with respect to FIGS. 10A-10D. Then, the 8 bit indexed color image is converted to a normalized RGB map RGB(i,j) with the color of each pixel being represented by (R, G, B) three values and each value range from 0~1. Each pixel of a RGB image is composed of three numbers (R, G, B) corresponding to the components of red, green and blue color. Each of the three numbers can range from 0~255 if 8 bit values are used or 0~1 if normalized values are used and the (R, G, B) will determine the color and brightness of the color in a pixel.

Referring now to FIG. 11C, both the anatomical (FIG. 11A) and physiological layers (FIG. 11B) are fused together by creating an 8 bit RGB color image represented by the following equation:

$$Img(i,j) = Img_A(i,j) \times RGB(i,j) \qquad \text{Eqn. (2)}$$

where $Img_A(i,j)$ for each color channel might be adjusted separately and differently to achieve optimal visualization effect. Thus, the image of FIG. 11A adjust brightness and the image of FIG. 11B adjusts color to provide the image of FIG. 11C, which is combination of both anatomy and physiology.

As discussed above, a near infra-red image/visible light image can visualize the surface and sub-surface anatomical structure of the vasculature of a tissue/organ. Blood flow measuring technologies, such as LSI, LDI or fluorescence, can quantify the speed of blood flow and perfusion, thus revealing the functionality of the vasculature of a tissue/organ. In certain clinical situations, visualization of both the anatomical structure and the functionally of tissue/organ vasculature is important. Thus, in some embodiments of the present inventive concept NIR images are used as one layer of the VFA image, which reveals anatomical structure of the targeting tissue/organ vasculature. The physiologic map of blood flow and perfusion quantified by, for example, LSI, LDI or fluorescence technology, is used as another layer of the VFA, which reveals functionality and physiology of the targeted tissue/organ vasculature. Embodiments of the present inventive concept are configured to adjust the colorization and transparency of the two layers and a final visualization (VFA image) is achieved, which represents both anatomy and functionality of the vascular system of a certain tissue/organ.

It will be understood that embodiments of the present inventive concept may be used in any format of clinical imaging, which includes both surgical imaging (usually an in-patient application) and other out-patient imaging procedure (non-surgical application) without departing from the scope of the present inventive concept.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed:

1. A method for combining anatomical data and physiological data on a single image, the method comprising:
   obtaining an image of a sample using a single camera, the image of the sample being at least one of a raw near-infrared (NIR) image of the sample or a visible light image of the sample including anatomical structure of the sample;
   obtaining a physiologic map of blood flow and perfusion of the sample; and
   combining the anatomical structure of the sample and the physiologic map of the sample into a single image of the sample, the single image of the sample displaying anatomy and physiology of the sample in the single image in real time,
   wherein the obtaining a physiologic map of blood flow and perfusion of the sample is carried out using laser speckle imaging (LSI); laser Doppler imaging (LDI); or a blood flow and perfusion angiography resemblance from a fluorescence image; and
   wherein at least one of the obtaining an image, obtaining a physiologic map and combining is performed by at least one processor.

2. The method of claim 1, wherein obtaining the image comprises obtaining the raw NIR image using a wavelength of from 780 nm to 2500 nm and/or obtaining the visible light image using a wavelength of from 400 nm to 700 nm.

3. The method of claim 1, wherein combining the anatomical structure of the image and the physiologic map of the sample into a single image comprises adjusting one or more properties of the raw NIR image and/or the visible light image and/or the physiologic map.

4. The method of claim 3:
wherein the one or more properties comprise at least one of colorization, transparency and a weight function; and
wherein the physiologic map illustrates one of blood flow and perfusion, flow distribution, velocity, and/or volume rate of blood flow (cc/min) quantification in primary vessels based on fluid dynamic modeling.

5. The method of claim 3, wherein combining further comprises creating an 8 bit RGB color image represented by the following equation:

$$Img(i,j)=Img_A(i,j) \times RGB(i,j)$$

wherein $Img_A(i,j)$ is an 8 bit gray scale visible image of the target tissue/organ, wherein i and j are pixel indexes along horizontal and vertical directions, respectively, and $Img_A(i,j)$ for each color channel is adjusted separately to achieve a desired visualization effect.

6. The method of claim 1:
wherein the sample comprises one of tissue and an organ; and
wherein the obtained image comprises anatomical structure of a vasculature of at least one of the tissue and the organ.

7. The method of claim 1, wherein obtaining the image is preceded by illuminating the sample with at least one light source, the method farther comprising reflecting a portion of light from the at least one light source to obtain the image and the physiologic map during a single data acquisition.

8. The method of claim 1, further comprising combining a plurality of images with a corresponding plurality of physiologic maps to provide a video displaying anatomy and physiology of the sample in real time.

9. A computer system for combining anatomical data and physiological data on a single image, the system comprising:
a processor; and
a memory coupled to the processor and comprising computer readable program code that when executed by the processor causes the processor to perform operations comprising:
obtaining an image of a sample using a single camera, the image of the sample being at least one of a raw near-infrared (NIR) image of the sample or a visible light image of the sample including anatomical structure of the sample;
obtaining a physiologic map of blood flow and perfusion of the sample; and
combining the anatomical structure of the sample and the physiologic map of the sample into a single image of the sample, the single image of the sample displaying anatomy and physiology of the sample in the single image in real time,
wherein the obtaining a physiologic map of blood flow and perfusion of the sample is carried out using laser speckle imaging (LSI); laser Doppler imaging (LDI); or a blood flow and perfusion angiography resemblance from a fluorescence image.

10. The system of claim 9, wherein obtaining the image comprises-obtaining the raw NIR image using a wavelength of from 780 nm to 2500 nm and/or obtaining the visible light image using a wavelength of from 400 nm to 700 nm.

11. The system of claim 9, wherein combining the anatomical structure of the image and the physiologic map of the sample into a single image comprises adjusting one or more properties of at least one of the raw NIR image or the visible light image and/or the physiologic map.

12. The system of claim 11, wherein the one or more properties comprise at least one of colorization, transparency and a weight function.

13. The system of claim 11, wherein combining further comprises creating an 8 bit RGB color image represented by the following equation:

$$Img(i,j)=Img_A(i,j) \times RGB(i,j)$$

wherein $img_A(i,j)$ is an 8 bit gray scale visible image of the target tissue/organ, wherein i and j are pixel indexes along horizontal and vertical directions, respectively, and $Img_A(i,j)$ for each color channel is adjusted separately to achieve a desired visualization effect.

14. The system of claim 9:
wherein the sample comprises one of tissue and an organ; and
wherein the obtained image includes anatomical structure of a vasculature of at least one of the tissue and the organ.

15. The system of claim 9, further comprising at least one illumination source configured to illuminate the sample, wherein a portion of light from the at least one source is reflected and used to obtain the image and the physiologic map during a single data acquisition.

16. The system of claim 9, wherein the processor farther performs operations comprising combining a plurality of images with a corresponding plurality of physiologic maps to provide a video displaying anatomy and physiology of the sample in real time.

17. A computer program product for combining anatomical data and physiological data on a single image, the computer program product comprising:
a non-transitory computer readable storage medium having computer readable program code embodied in the medium, the computer readable program code comprising:
computer readable program code to obtain an image of a sample using a single camera, the image of the sample being at least one of a raw near-infrared NIR) image of the sample or a visible light image of the sample including anatomical structure of the sample;
computer readable program code to obtain a physiologic map of blood flow and perfusion of the sample; and
computer readable program code to combine the anatomical structure of the image and the physiologic map of the sample into a single image of the sample, the single image of the sample displaying anatomy and physiology of the sample in the single image in real time,
wherein the obtaining a physiologic map of blood flow and perfusion of the sample is carried out using laser speckle imaging (LSI); laser Doppler imaging (LDI); or a blood flow and perfusion angiography resemblance from a fluorescence image.

18. The computer program product of claim 17, wherein the computer readable program code to obtain comprises computer readable program code to obtain the raw NIR image using a wavelength of from 780 nm to 2500 nm, and the visible light image using a wavelength of from 400 nm to 700 nm.

19. The computer program product of claim 18, wherein the computer readable program code to combine the anatomical structure of the image and the physiologic map of the sample into a single image comprises computer readable program code to adjust one or more properties of at least one of the raw NIR image or the visible light image and/or the physiologic map.

20. The computer program product of claim 19, wherein the one or more properties comprise at least one of colorization, transparency and a weight function.

21. The computer program product of claim 19, wherein the computer readable program code to combine further comprises computer readable program code to create an 8 bit RUB color image represented by the following equation:

$$Img(i,j) = Img_A(i,j) \times RGB(i,j)$$

wherein $img_A(i,j)$ is an 8 bit gray scale visible image of the target tissue/organ, wherein and j are pixel indexes along horizontal and vertical directions, respectively, and $Img_A(i,j)$ for each color channel is adjusted separately to achieve a desired visualization effect.

22. The computer program product of claim 17, wherein the sample comprises one of tissue and an organ, the computer program product further comprising computer readable program code to obtain an image including anatomical structure of the vasculature of at least one of the tissue and the organ.

23. The computer program product of claim 17, wherein the sample is illuminated with at least one source and wherein a portion of light from the at least one source is reflected to obtain the image and the physiologic map during a single data acquisition.

24. The computer readable program code of claim 17, further comprising computer readable program code to combine a plurality of images with a corresponding plurality of physiologic maps to provide a video displaying anatomy and physiology of the sample in real time.

25. The method of claim 1, wherein the method is a non-invasive method.

26. The system of claim 9, wherein the obtained images are non-invasive images.

* * * * *

UNITED STATES PATENT AND TRADEMARK OFFICE
CERTIFICATE OF CORRECTION

PATENT NO. : 10,722,173 B2
APPLICATION NO. : 15/518548
DATED : July 28, 2020
INVENTOR(S) : Cheng Chen et al.

Page 1 of 1

It is certified that error appears in the above-identified patent and that said Letters Patent is hereby corrected as shown below:

On the Title Page

Page 4, Column 2, item (56), change "LeSniok et al." to -- Lesnick et al. --.

In the Claims

Column 15, Line 37, change "farther" to -- further --.

Column 16, Line 19, change "img" to -- Img --.

Column 16, Line 36, change "farther" to -- further --.

Column 16, Line 50, change "NIR)" to -- (NIR) --.

Column 17, Line 1, change "nm," to -- nm --.

Column 17, Line 17, change "RUB" to -- RGB --.

Column 17, Line 20, change "img" to -- Img --.

Signed and Sealed this
Twenty-fifth Day of August, 2020

Andrei Iancu
*Director of the United States Patent and Trademark Office*